United States Patent [19]

Hogan

[11] 4,131,801
[45] Dec. 26, 1978

[54] X-RAY CRADLE TOP WITH TILTING MECHANISM

[75] Inventor: William F. Hogan, Woodbury, N.J.

[73] Assignee: Spectrum X-Ray Corporation, Westville, N.J.

[21] Appl. No.: 829,665

[22] Filed: Sep. 1, 1977

[51] Int. Cl.² .................... A47F 5/12; F16F 15/00
[52] U.S. Cl. ............................. 250/439 R; 108/6; 248/358 R
[58] Field of Search ............... 250/439, 456; 269/322, 269/323; 248/358 R, 329, 334; 188/67, 129; 108/6, 7, 8

[56] References Cited

U.S. PATENT DOCUMENTS

| | | | |
|---|---|---|---|
| 2,704,199 | 3/1955 | Olson | 74/520 |
| 3,588,500 | 6/1971 | Koerner | 250/439 |
| 3,949,624 | 4/1976 | Beinert | 74/520 |

*Primary Examiner*—Alfred E. Smith
*Assistant Examiner*—T. O'Hare
*Attorney, Agent, or Firm*—Paul & Paul

[57] ABSTRACT

A cradle top for an X-ray examination table carries a cradle or basket which is rotatable about its lengthwise axis. The cradle top is mounted for movement in the elevational, lengthwise and transverse directions. The cradle top is also connected to a scissors linkage mechanism for tilting angulation. A ball nut damping device prevents oscillatory movement or "bounce" of the patient as he or she is raised and lowered to and from the tilted position.

4 Claims, 7 Drawing Figures

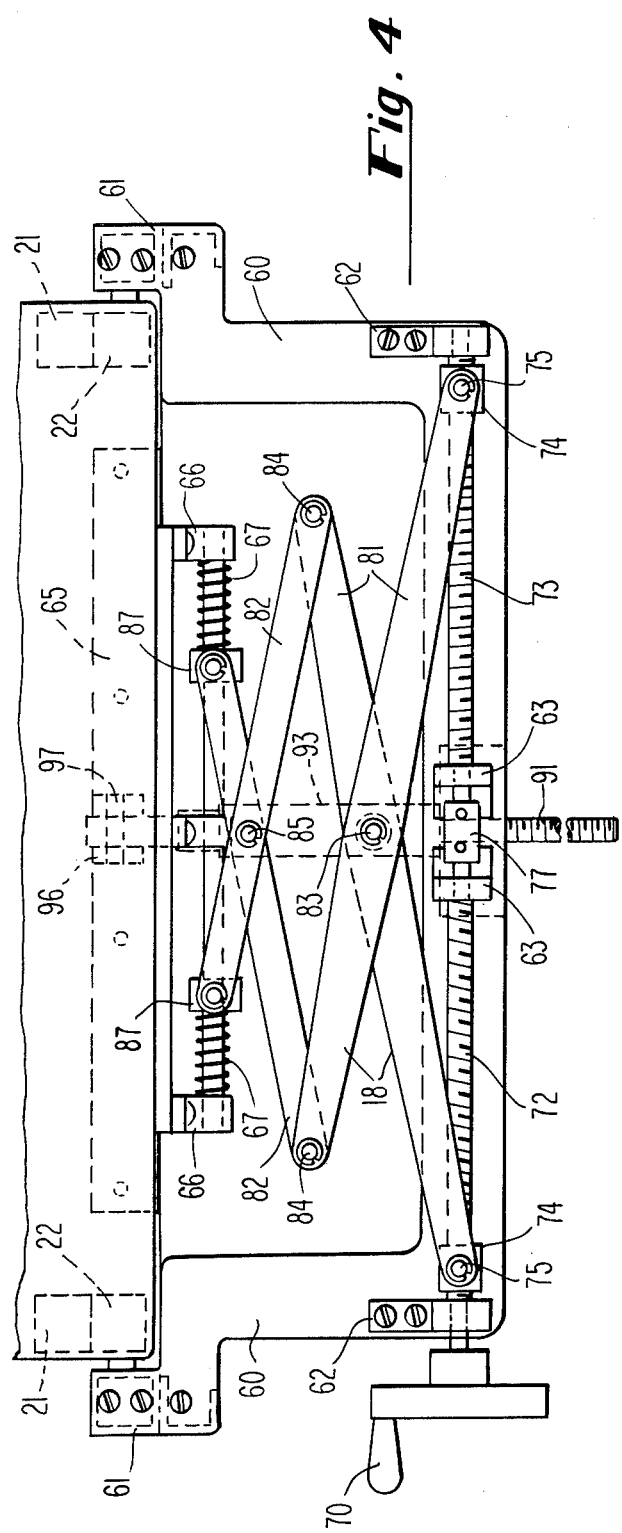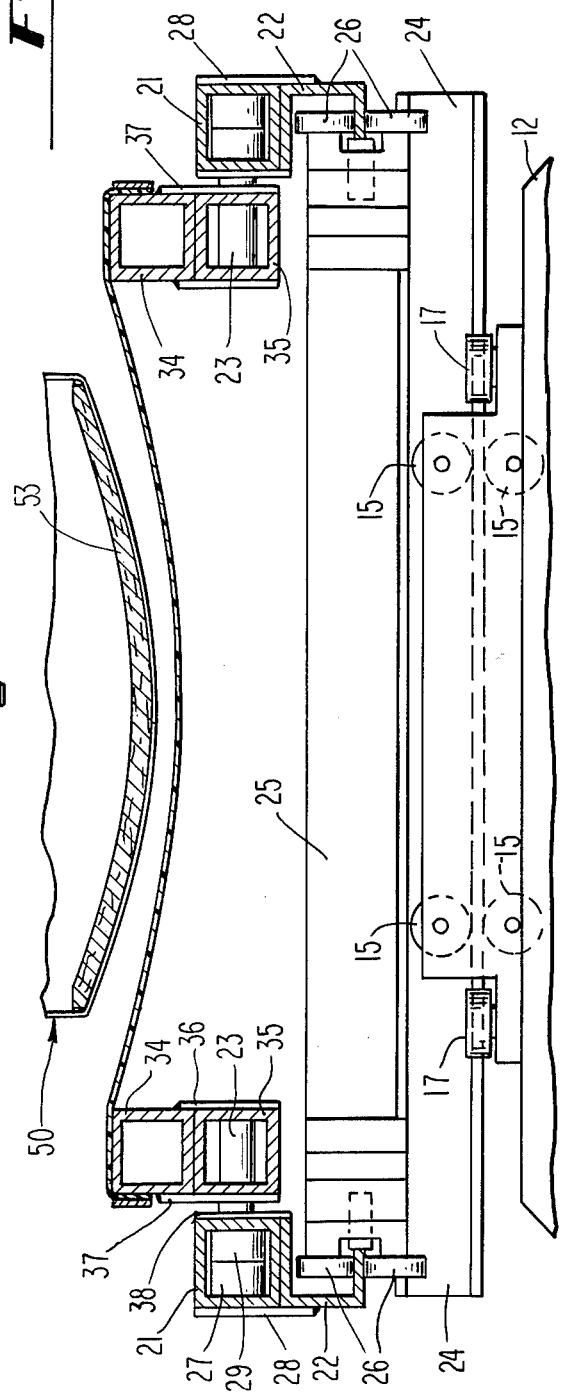

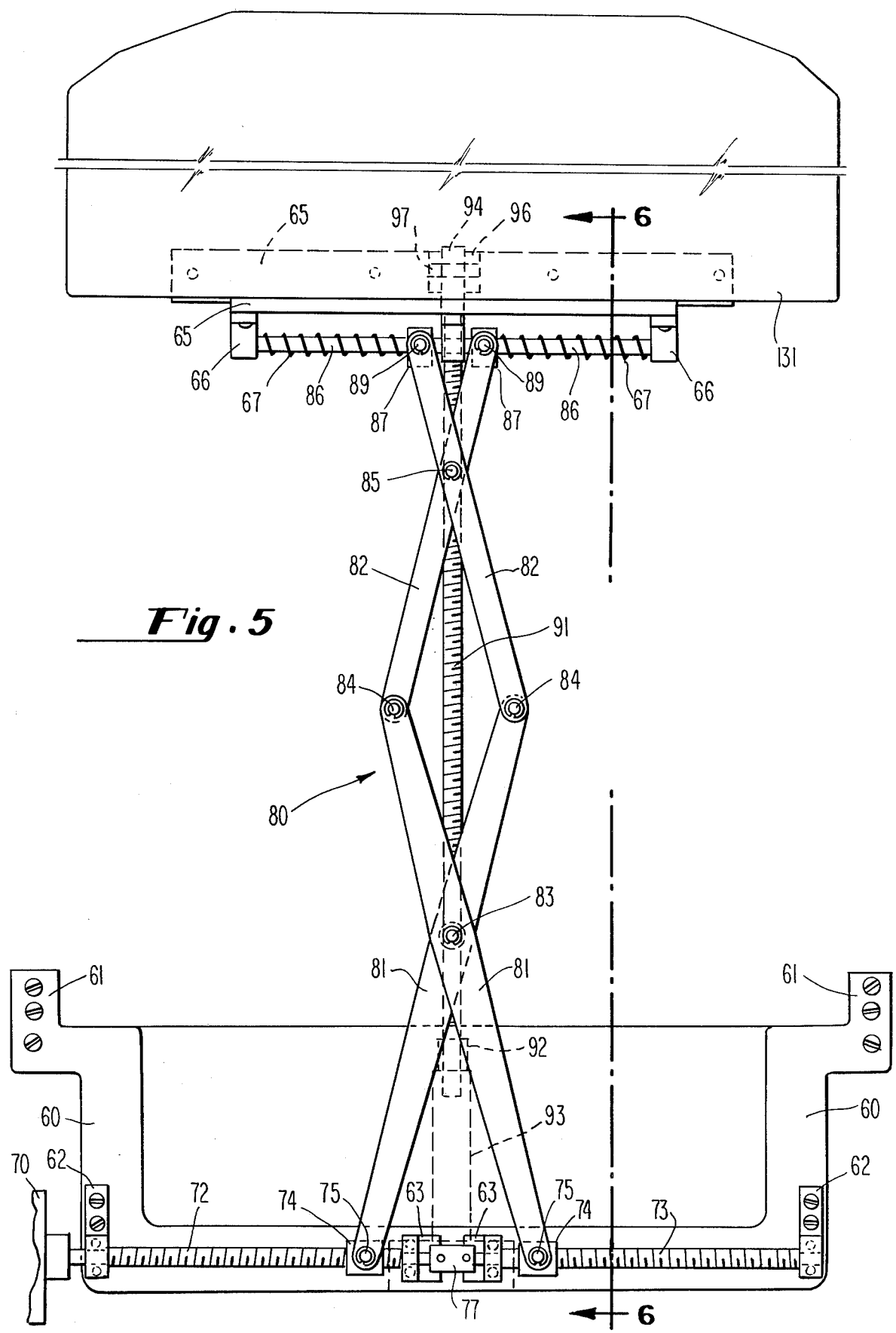

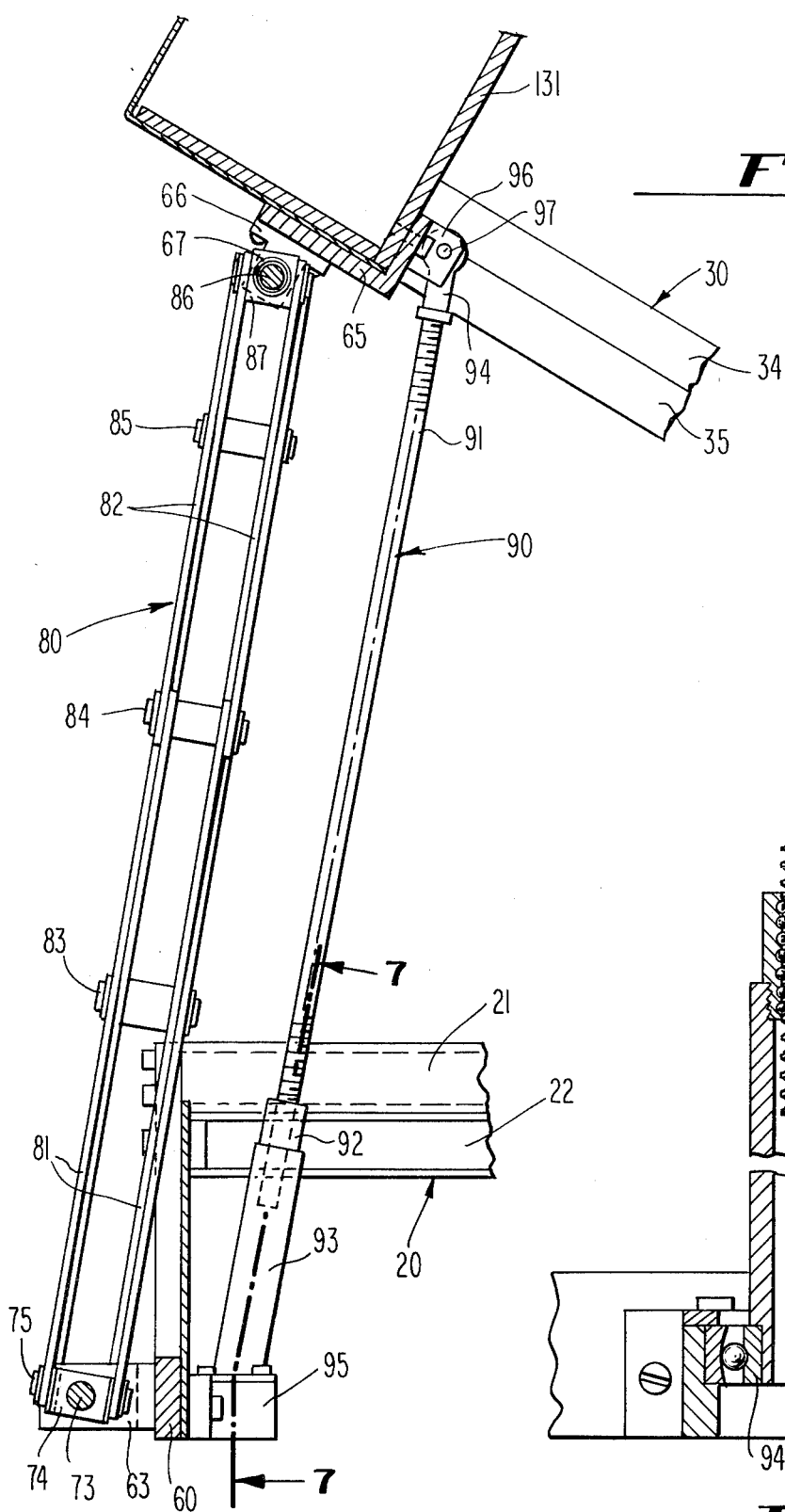
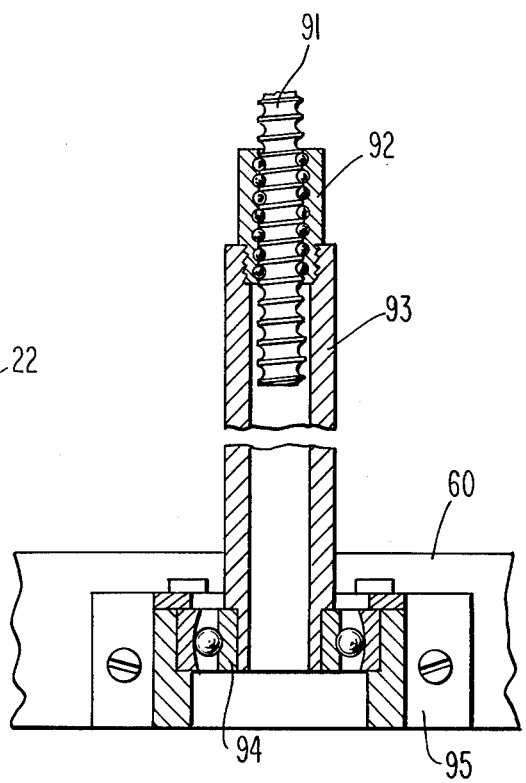
Fig. 6
Fig. 7

X-RAY CRADLE TOP WITH TILTING MECHANISM

RELATED APPLICATIONS

The scissors linkage and damping mechanisms disclosed in the present application represents a modification of, and an improvement over, the sprocket-and-chain drive mechanism shown in my co-pending patent application, Ser. No. 758,475, filed Jan. 11, 1977, entitled X-Ray Cradle Top with Tilting Mechanism.

BACKGROUND OF THE INVENTION

This invention relates to X-ray examination work and in particular to cardiology X-ray examination.

The heart has two valves which occupy positions which are inclined approximately 30° from the vertical. As a result, X-rays which pass vertically through the patient do not pass properly through these two heart valves and their vessels, and, in order to obtain the desired X-ray pictures of these heart valves and their vessels, it has been customary in the prior art to tilt the X-ray apparatus and the image-receiving apparatus approximately 30° from the vertical. By providing a tiltable table top for the patient-receiving rotatable cradle or basket, the need for tilting the X-ray projecting and image-receiving apparatus for cardiology examination is avoided, according to the present invention.

SUMMARY OF THE INVENTION

A principal purpose of the present invention is to provide an X-ray examination table for cardiology X-ray examination work which avoids the need for tilting the X-ray projecting and image-receiving apparatus away from the vertical in order to obtain desired X-ray pictures of heart valves and their vessels.

The forgoing object is accomplished, in accordance with the present invention, by providing an axially rotatable patient-receiving basket or cradle which is so mounted on a cradle top that, in addition to being elevatable and movable translationally in both the lengthwise and lateral directions, it is tiltable about its short transverse axis to a position at least 30° from the horizontal. Tilting of the cradle provides for convenient perpendicular visualization in the oblique half-axial position of the left interior descending coronary artery and its branches with minimal patient longitudinal centering adjustment necessary during angulation. Angulation of the patient is accomplished safely and quickly with a simple manual crank handle located at the head end of the table. The technician from this location may, at the option of the operator, also control rotation and recentering of the patient-holding cradle. Oscillation or "bounce" of the patient cradle during angulation is prevented by a ball nut damping device. When the cradle top tilt mechanism is used in conjunction with a desired form of undertable X-ray tube motor drive, the X-ray tube is automatically raised and lowered as the cradle is tilted to its angular position and brought back to horizontal, keeping to a minimum the patient's focal-spot distance change.

BRIEF DESCRIPTION OF THE DRAWINGS

In FIG. 1, the table top is shown in untilted position.

FIG. 3 is a view, in section, looking to the right along the line 3—3 of FIG. 1.

FIG. 4 is an end elevation view looking along the line 4—4 of FIG. 1.

FIG. 5 is an end elevational view looking along the line 5—5 of FIG. 2.

FIG. 6 is a side elevational view of the scissors linkage mechanism looking along the line 6—6 of FIG. 5.

FIG. 7 is a detailed view looking along the line 7—7 of FIG. 6.

DETAILED DESCRIPTION OF THE PREFERRED EMBODIMENTS

Figure 1:
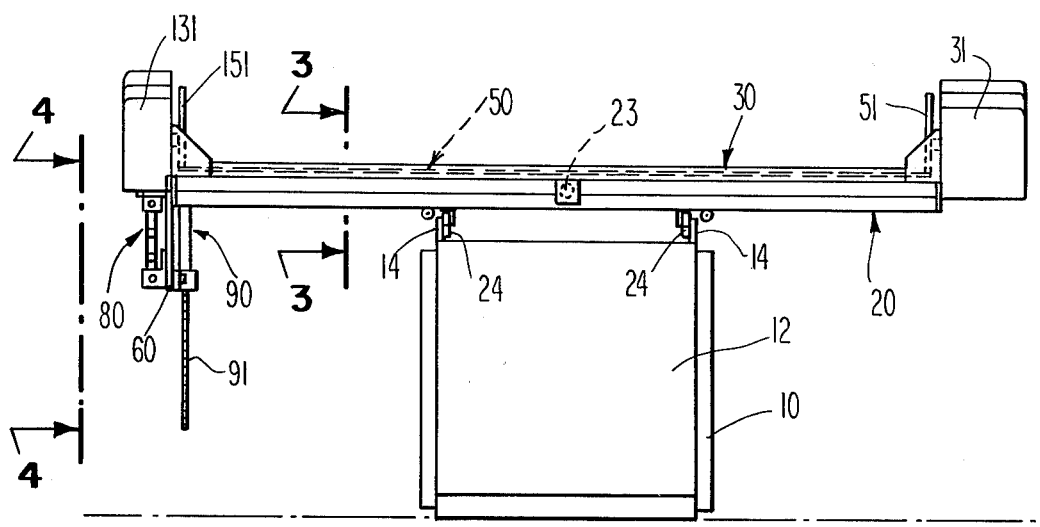
FIG. 1 is a simplified side elevational view of an X-ray examination table provided with a table top tilting mechanism of the scissors linkage type in accordance with the present invention.
Figure 2:
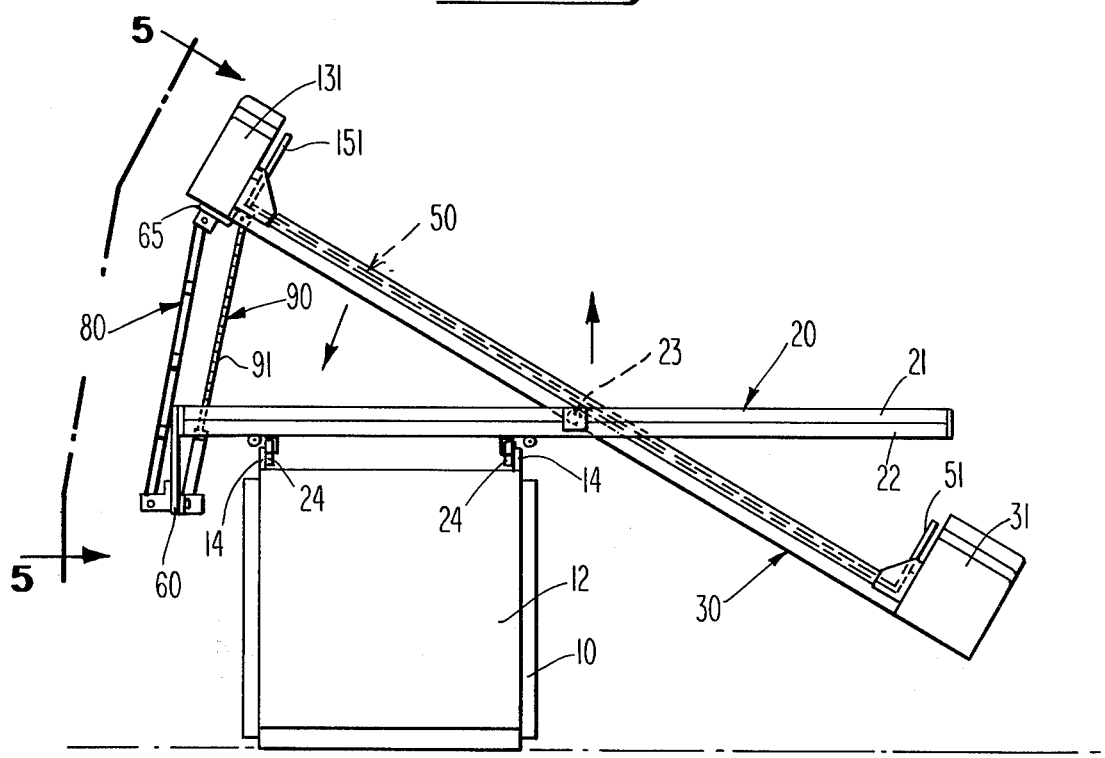
FIG. 2 is simplified view similar to FIG. 1 but showing the table top in tilted position.

Referring now to FIGS. 1 and 2, there is shown in side elevation a simplified illustration of a tilting table top adapted for cardiology X-ray examination. A generally rectangular pedestal or base 10 has therein an interior elevator 12 which supports a non-tilting table frame 20. Frame 20 supports, for pivotal movement within the frame, a tilting table top 30 which carries a rotatable cradle or basket 50 in which the patient is placed and strapped for X-ray examination. Supported at the head end of the non-tilting table frame 20 is an angulation or tilt mechanism 80 by means of which the pivotal table top 30 is moved angularly between the horizontal position illustrated in FIG. 1 and an inclined position such as is illustrated in FIG. 2 in which the head end of the table top 30 is elevated and the foot end is lowered. The angulation mechanism 80 is designed to provide a maximum angle of inclination of the order of 30° from the horizontal, thereby to provide for perpendicular X-ray visualization of the oblique half-axial position of the left interior descending coronary artery and its branches. A ball nut damping device prevents oscillation or bounce of the patient during angulation.

The base or pedestal 10 is of known construction and so is the interior elevator 12. Elevator 12 may preferably contain a motor driven raising jackscrew drive and an under table X-ray tube and collimator which is raised when the non-tilting table frame 20 is raised thereby to maintain constant the patient focal distance in relationship to the image receptor located above the table top.

The non-tilting table frame 20 in addition to being raised and lowered by the interior elevator 12 is movable transversely and also longitudinally on the elevator 12. As seen in FIG. 3, transverse movement is provided by four pairs of rollers 15. Two of the pairs of rollers 15 are mounted on a cross-bar 14 fixed to the top of elevator 12 at the left edge and the other two pairs are mounted on a similar cross-bar 14 (FIGS. 1-2) fixed to the right edge of the elevator top. Each pair comprises an upper roller and a lower, as seen in FIG. 3, which shows the forward and rearward pairs of rollers 15 on the left cross-bar 14. Also mounted on the cross-bars 14 are guide rollers, such as rollers 17 seen in FIG. 3.

For transverse movement, table top 20 is mounted on a pair of cross-channel members 24 (FIGS. 1-2) one of which is seen in FIG. 4. The horizontal lower flanges of the channel members 24 are received between the upper and lower rollers of the roller pairs 15. Thus, channel members 24, and the structure which is supported on channel members 24, are movable as a unit back and forth on the elevator 12.

The non-tilting table frame 20 is also movable in its lengthwise direction. The means that provide for lengthwise direction are best seen in FIG. 3. Supported on each of the members 24 is a cross-member 25 to the opposite ends of which are mounted pairs of rollers 26. There are four sets of such pairs of rollers, two sets of forward rollers and two pairs of rearward rollers. One set of each is visible in FIG. 3. Rollers 26 are carried transversely when the non-tiltable table frame 20 including cross-frame members 24, 25, is moved transversely on rollers 15. Rollers 26 do not move lengthwise. These rollers support the table frame 20 for movement in its lengthwise direction.

At each side of the non-tiltable table frame 20 is a lengthwise extending beam or tube 21 of hollow square cross-section. Secured, as by welding to the underside of each of the square tubes 21, is an elongated C-shaped member 22. The lower leg of each of the C-members 22 is received between the paired rollers 26 and is supported on the lower of the rollers. By the means just described, the table frame 20, comprising the beam members 21 and 22, is movable in its lengthwise direction on the four sets of paired rollers 26. The lengthwise-extending beam members 21, 22, are connected at their ends by cross-members 23.

According to the present invention, a table top 30 carrying a patient rotator basket 50 is mounted for pivotal inclination or angulation within the frame 20. The means provided for achieving angulation are designed to tilt the table top 30 and its rotatable basket 50 in a safe and controlled manner so that the patient may be examined in any position between the horizontal and a position which is inclined at an angle of approximately 30° relative to the horizontal.

The scissors-linkage drive mechanism for tilting the table top 30 and basket 50 is at the head end of table frame 20 and is identified generally by the reference numeral 80.

Table top 30 includes, at each side, an elongated beam 35 which extends the full length of the table top. Beams 35 are tubular, being of hollow square cross section. Supported on the top of the tubular beams 35 at each side of the frame 30 are elongated hollow square tubes 34. Supported across the opposite ends of table top 30, on or at the opposite ends of the lengthwise extending beams 34 are housing 131 at the head end and housing 31 at the foot end. Projecting axially inwardly from each of the end housings 131 and 31 is a short shaft or trunnion, and supported for rotation on the trunnions is the rotatable cradle or basket 50 having end panels 151 and 51. Supported therebetween is an arcuate or dished panel 53 (FIG. 3) on which the patient is supported.

The manner in which the table top 30 is mounted for pivotal tilting about its transverse center axis within the non-tilting frame 20 will now be described. The central pivot means at each side of the frame 20 are seen in detail in FIG. 3. The means at each side are similar and thus it will be necessary to describe the means at but one of the sides. A pivot pin or stud 23 is inserted into square tube 35 which extends the full length of the tiltable table top 30. Pivot pin 23 is inserted from the inward side of square tube 35 into a pair of bushings 27, 29 which are within the square tube 21 which extends the full length of the non-tiltable frame 20 and which is supported on the C-member 22. Plates 28 and 38 secure the bushings 27 and 29. Plates 36 and 37 support the pivot pin 23.

The means by which the tiltable table top 30 carrying the patient cradle 50 is moved from the horizontal position shown in FIG. 1 to the angulated or tilted position shown in FIG. 2 will now be described.

The means employed to accomplish angulation or tilting consists essentially of a scissors linkage identified 80, plus damping means to avoid the undulations or bounce which the patient would otherwise be subjected to as he is cranked from a horizontal to a tilting position, and vice versa. In FIG. 4, the scissors linkage mechanism 80 is shown in retracted condition, which is the condition of the scissors mechanism when the table top 30 is in horizontal position. In FIG. 5, the scissors linkage mechanism 80 is shown in extended condition, which is the condition of the scissors mechanism when the table top 30 is in fully tilted position, as illustrated in FIG. 2. FIG. 6 is a side elevational view of the scissors mechanism 80 in fully extended position. The anti-bounce means, identified 90, is seen best in FIGS. 5–7.

The scissors linkage mechanism 80 is supported in a large U-shaped bracket 60 having ears 61 which are connected to the underside of the non-tiltable frame 20 at the head end of the X-ray table top. Secured to the lower portion of bracket 60 are a pair of bearing blocks 62 which support a pair of elongated coaxially-aligned screw shafts 72 and 73 which are connected together at their inward ends by a coupling 77. Bearing blocks 63 support the inward ends of the screw shafts. One of the screw shafts carries a right-hand thread; the other carries a left-hand thread. Screws 72, 73 could, however, be one integral screw shaft having right-hand and left-hand thread sections, so far as operation is concerned. Threaded on screw shafts 72, 73 are a pair of rectangular nuts 74 and extending in opposite directions from each nut 74 is a short lateral pivot shaft 75 on which the lower ends of arms 81 of the scissors linkage mechanism 80 are supported. The arms 81 are retained on the pivot shafts 75 by retaining clips 76. Mounted on the outward end of screw shaft 72 is a crank 70 by means of which the screws 72 and 73 are rotated.

As seen best in FIG. 6, the arms of the scissors linkage mechanism 80 comprise pairs of spaced-apart parallel arms. In the particular mechanism shown in the drawings, there are two pairs of lower arms 81 and two pairs of upper arms 82. The lower ends of arms 81 are pivotally connected to pivot shafts 75 of nuts 74. The upper ends of arms 81 are connected pivotally to the lower ends of upper arms 82 by spacer pivot pins 84. The scissors arms are retained on the spacer pins by snap rings. The two pairs of lower scissors arms 81 are pivotally connected at their intermediate points by spacer pins 83, with snap rings employed as retaining elements. The two pairs of upper scissors arms 82 are pivotally connected at their intermediate points by spacer pivot pin 85. Again snap rings are employed to retain the scissors arms on the spacer pin.

The upper ends of the pairs of upper scissors arms 82 are pivotally connected to short pivot shafts 89 which project laterally from ball bushing housings 87. Housings 87 are freely mounted for sliding movement on non-threaded guide shaft 86. Guide shaft 86 is supported in a pair of mounting blocks 66 which are secured, as by bolts, to a bracket 65 which is secured to the inside cover plate of end housing 131. A pair of compression springs 67 are mounted on guide shaft 86 between the mounting blocks 66 and the free-sliding ball bushing housings 87. These springs 67 thrust against the bearing housings 87 urging them inwardly in opposing directions toward each other.

If no damping or anti-bounce mechanism were incorporated into the scissors-type tilting mechanism, the patient in the cradle would be subjected to vertical oscillation or bounce as the operator turned crank 70 to lift the patient from the horizontal position (FIG. 1) to the inclined position (FIG. 2) or to lower the patient from the inclined to the horizontal position. To subject the patient to such oscillatory movement or bounce is, of course, undesirable and, accordingly, an anti-bounce or damping mechanism has been incorporated into the scissors tilt mechanism of the present invention. Such damping mechanism may also have other applications, as will be mentioned later.

As seen best in FIGS. 6 and 7, the anti-bounce or damping mechanism 90 includes an elongated non-rotatable threaded rod 91 which is secured pivotally at its upper end to end housing 131 by means of an end fitting 94 pinned on pivot pin 97 in mounting bracket 96 which is secured to angle bracket 65. Threaded on the lower end of rod 91 is a ball nut 92 having a downward extension 93. As shown in detail in FIG. 7, ball nut 92 is secured, as by screwing, into the upper end of the extension 93, and the lower end of the extension 93 is fitted into the inner race of a universal bearing 94 which is supported in a bracket 95 secured to bracket 60. When the attendant rotates crank 70 to lift the head end 131 of the tiltable table top 30 from the horizontal to the inclined position, the upward movement of the table-top end 131 pulls rod 91 upwardly through the ball nut 92, and the ball nut 92 and its extension 93 are caused to rotate rapidly in universal bearing 94, and the normal tendency of end 131 of table top 30 to oscillate as the crank 70 is rotated is damped out by the action of ball nut 92 and extension 93. Similarly, when the patient is returned from the tilted to the horizontal position, the downward movement of end 131 of the table top 30 pushes the threaded rod 91 down through the ball nut 92, and the ball nut and its extension are caused to rotate briefly, in the opposite direction from that in which they rotated during the upward movement.

The explanation of why the ball nut 92 is capable of smoothing out what would otherwise be a bouncy ride by the patient as he or she is raised to, and lowered from, the tilted position, is believed to reside in the fact that the ball nut, rotating rapidly in one direction in response to an axial force in one direction, is unable to stop and reverse its rotational direction in sufficient time to respond to a momentary force in the opposite axial direction. Thus, rod 91 is prevented by ball nut 92 from following the oscillations or bounce of the scissors mechanism as it lifts or lowers the head end 131 of the table top 30.

The damping mechanism disclosed is of particular importance in preventing patient bounce during cardiology X-ray examination. However, the damping mechanism is not limited to such use. It is believed to have substantially broader application.

What is claimed is:

1. Apparatus for supporting a tiltable load, said apparatus comprising;
    a. a non-tiltable frame;
    b. a tiltable load member;
    c. pivotal means for mounting said load member on said frame for tilting movement about the transverse axis of said load member;
    d. a scissors-linkage mechanism for tilting said load member;
    e. means mounting one end of said scissors-linkage mechanism at one end of said non-tiltable frame;
    f. means connecting the other end of said scissors-linkage mechanism to one end of said tiltable load member;
    g. drive means for extending and retracting said scissors-linkage mechanism to raise and lower said one end of said load member; and
    h. damping means for preventing oscillation of said load member during extension and retraction of the scissor-linkage mechanism, said damping means comprising;
    h-1 an elongated threaded rod;
    h-2 means pivotally connecting the upper end of said threaded rod to said one end of said tiltable load member;
    h-3 ball nut means on a lower portion of said threaded rod;
    h-4 bearing means mounting said ball nut means at said one end of said non-tiltable frame, wherein when said scissors-like mechanism is moved toward its extended position, said rod is pulled toward an extended position causing said ball nut means to rotate on said rod, and wherein when said scissor-like mechanism is moved toward its retracted position, said rod is pulled downwardly, causing said ball nut means to rotate in the opposite direction on said rod.

2. Apparatus according to claim 1 wherein said drive means includes:
    a. a screw shaft having right-hand threads along one section at one end of said shaft and left-hand threads along another section at the opposite end of said screw shaft;
    b. a pair of nuts, one nut on each threaded section of said screw shaft;
    c. means pivotally connecting one end of said scissors-linkage mechanism to said pair of nuts;
    d. a guide shaft supported at one end of said load member;
    e. a pair of bearing blocks slideably mounted on said guide shaft;
    f. means pivotally connected the upper end of said scissors-linkage mechanism to said slideable bearing blocks; and
    g. means for rotating said screw shaft to cause said nuts to move toward or away from each other according to the direction of rotation, thereby to extend or retract said scissors-linkage thereby to raise and lower said one end of said tiltable load member.

3. Apparatus for supporting a patient for X-ray examination, said apparatus comprising:
    a. a pedestal base;
    b. an elongated non-tiltable table frame;
    c. support means supporting said table frame horizontally on said base and adapted for moving said frame in the transverse and lengthwise directions relative to said base;
    d. an elongated tiltable table top;
    e. pivotal means for mounting said table top on said frame for tilting movement about its transverse axis;
    f. a cradle for receiving a patient for X-ray examination;
    g. support means for supporting said cradle on said table top;
    h. a scissors-linkage mechanism for tilting said table top;

i. means mounting one end of said scissors-linkage mechanism at one end of said non-tiltable table frame;
j. means connecting the other end of said scissors-linkage mechanism to one end of said tiltable table top;
k. drive means for extending and retracting said scissors-linkage mechanism to raise and lower said one end of said table top; and
l. damping means for preventing oscillation of the table top during extension and retraction of the scissors-linkage mechanism, said damping means comprising;
l-1. an elongated threaded rod;
l-2. means pivotally connecting the upper end of said threaded rod to one end of said tiltable table top;
l-3. ball nut means on a lower portion of said threaded rod;
l-4. bearing means mounting said ball nut means at said one end of said non-tiltable table frame, wherein when said scissors-like mechanism is moved toward its extended position, said rod is pulled toward an extended position causing said ball nut means to rotate on said rod, and wherein when said scissor-like mechanism is moved toward its retracted position, said rod is pulled downwardly, causing said ball nut means to rotate in the opposite direction on said rod.

4. Apparatus according to claim 3 wherein said drive means includes;
a. a screw shaft having right-hand threads along one section at one end of said shaft and left-hand threads along another section at the opposite end of said screw shaft;
b. a pair of nuts, one nut on each threaded section of said screw shaft;
c. means pivotally connecting one end of said scissors-linkage mechanism to said pair of nuts;
d. a guide shaft supported at said one end of said table top;
e. a pair of bearing blocks slideably mounted on said guide shaft;
f. means pivotally connecting the upper end of said scrissors-linkage mechanism to said slideable bearing blocks; and
g. means for rotating said screw shaft to cause said nuts to move toward or away from each other according to the direction of rotation, thereby to extend or retract said scissors-linkage, thereby to raise and lower said one end of said tiltable table top.

* * * * *

UNITED STATES PATENT OFFICE
CERTIFICATE OF CORRECTION

Patent No. 4,131,801  Dated December 26, 1978

Inventor(s) William F. Hogan

It is certified that error appears in the above-identified patent and that said Letters Patent are hereby corrected as shown below:

Column 5, line 37, "briefly" should read -- rapidly --.

Signed and Sealed this

Twenty-fourth Day of April 1979

[SEAL]

Attest:

RUTH C. MASON
Attesting Officer

DONALD W. BANNER
Commissioner of Patents and Trademarks